United States Patent [19]

Van Heertum et al.

[11] Patent Number: 4,531,967
[45] Date of Patent: Jul. 30, 1985

[54] SUBSTITUTED PHENYLALKYL QUINCLIDINUM SALTS AND THEIR USE AS PLANT GROWTH CONTROL AGENTS

[75] Inventors: John C. Van Heertum, Concord; Maria P. Herrero, Berkeley, both of Calif.

[73] Assignee: The Dow Chemical Company, Midland, Mich.

[21] Appl. No.: 541,769

[22] Filed: Oct. 13, 1983

[51] Int. Cl.³ ............... A01N 43/40; C07D 453/02
[52] U.S. Cl. ........................... 71/94; 546/133; 546/137
[58] Field of Search .............. 546/133, 137; 71/94

[56] References Cited

U.S. PATENT DOCUMENTS

| | | | |
|---|---|---|---|
| 3,277,118 | 10/1966 | Schmid et al. | 549/492 |
| 3,539,632 | 11/1970 | Morris | 71/121 X |
| 4,343,647 | 8/1982 | Dunbar et al. | 71/76 |

OTHER PUBLICATIONS

Gandler, J. et al., *J. Am. Chem. Soc.*, 1982, 104, 1937-1951.
Chemical Abstracts, 81:119807f, (1974), [Pullman, B., et al., C.R. Acad. Sci., Ser. D, 1974, 278(13), 1785-1788].
Chemical Abstracts, 72:100465k, (1970), [Nielson, A., J. Heterocycl. Chem., 1970, 7(1), 231-234].
Chemical Abstracts, 73:65596a, (1970), [McKenna, J., et al., J. Chem. Soc., D, 1970, (14), 867].
Chemical Abstracts, 72:132482e, (1970), [Grob, C., et al., Helv. Chim. Acta, 1970, 53(3), 613-617].

*Primary Examiner*—Richard A. Schwartz
*Attorney, Agent, or Firm*—S. Preston Jones; Ronald G. Brookens

[57] ABSTRACT

Compounds are prepared which correspond to the formula

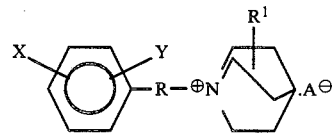

wherein
R represents methylene, ethylene or ethylidene;
$R^1$ represents hydrogen, hydroxy, chloro, bromo, fluoro, iodo, cyano, —$COOR^2$, oxo or acetoxy;
Y represents hydrogen, chloro, bromo, iodo or fluoro;
X represents hydrogen, alkyl of 1 to 6 carbon atoms, alkoxy of 1 to 6 carbon atoms, alkylthio of 1 to 6 carbon atoms, alkenyloxy of 2 to 6 carbon atoms, alkynyloxy of 2 to 6 carbon atoms, cyano, trifluoromethyl, (trifluoromethyl)thio, (trifluoromethyl)sulfonyl, trifluoromethoxy, —$COOR^2$ wherein $R^2$ is alkyl of 1 to 6 carbon atoms, —$C(O/S)NR^3R^4$ wherein $R^3$ represents $R^2$, alkenyl of 2 to 6 carbon atoms or alkynyl of 2 to 6 carbon atoms and $R^4$ represents $R^3$ or hydrogen, or —$S(O)_2NR^2R^3$ with the proviso that X and Y cannot both be hydrogen at the same time and A represents a non-phytotoxic anion. The compounds have been found to be active plant growth enhancers.

35 Claims, No Drawings

SUBSTITUTED PHENYLALKYL QUINCLIDINUM SALTS AND THEIR USE AS PLANT GROWTH CONTROL AGENTS

BACKGROUND OF THE INVENTION

One active area of agricultural research is devoted to the production of more productive plant life, particularly that plant life usually considered as or associated with food sources or beauty for man. In this research, much effort has been expended in developing means for the regulation of the growth pattern of plant life, particularly as evidenced by the retardation of growth and/or the enhancement of maturation.

These objectives have been accomplished, in part, by the discovery, development and distribution of various chemical agents which alter or modify the growth characteristics of plants. Documentation of such can be found in Dwarfing Plants With Chemicals, Agricultural Research Service, U.S. Dept. of Agriculture, January 1961.

PRIOR ART

Various ammonium salts have been employed in the control of plant growth. For example, substituted benzyltrialkylammonium salts are taught in U.S. Pat. No. 4,343,647. The compound diethylmethyl (2-phenylallyl)ammonium iodide is taught in U.S. Pat. No. 3,539,632. Substituted benzyltrialkylammonium halides are taught in U.S. Pat. No. 2,772,310. Various quaternary ammonium fluorides are taught in U.S. Pat. No. 3,277,118.

SUMMARY OF THE INVENTION

The present invention is directed to compounds corresponding to the general formula

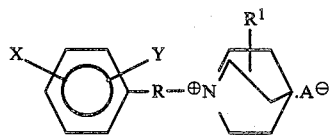

R represents methylene, ethylene or ethylidene;
$R^1$ represents hydrogen, hydroxy, chloro, bromo, fluoro, iodo, cyano, —$COOR^2$, oxo or acetoxy;
Y represents hydrogen, chloro, bromo, iodo or fluoro;
X represents hydrogen, alkyl of 1 to 6 carbon atoms, alkoxy of 1 to 6 carbon atoms, alkylthio of 1 to 6 carbon atoms, alkenyloxy of 2 to 6 carbon atoms, alkynyloxy of 2 to 6 carbon atoms, cyano, trifluoromethyl, (trifluoromethyl)thio, (trifluoromethyl)sulfonyl, trifluoromethoxy, —$COOR^2$ wherein $R^2$ is alkyl of 1 to 6 carbon atoms, —$C(O/S)NR^3R^4$ wherein $R^3$ represents $R^2$, alkenyl of 2 to 6 carbon atoms or alkynyl of 2 to 6 carbon atoms and $R^4$ represents $R^3$ or hydrogen, or —$S(O)_2NR^2R^3$ with the proviso that X and Y cannot both be hydrogen at the same time and A represents a non-phytotoxic anion.

In the present specification and claims, the term "alkyl" is employed to designate straight chained alkyl groups of 1 to 6 carbon atoms or branched or cyclic alkyl groups containing from 3 to 6 carbon atoms. These groups can contain from 1 to 6 chloro, bromo, fluoro or iodo atoms.

The compounds of the above formula have been found to be active in increasing (i.e., enhancing) or reducing the linear growth of various plants. The compounds are particularly effective in altering the growth pattern of many plants such as food crops, ornamental plants and various trees.

Some of the typical effects obtained by treating plants with the plant growth control of the present invention include an increase in the plant height and/or weight and/or stalk diameter, a reduction of the plant height and size, stimulation of seed germination, increased flowering and/or induction of flowering, an increase in yield of fruit and an increase in photosynthesis.

As indicated above, it is possible to employ plant growth control agents to influence the plants' natural growth rhythm. The particular effect which occurs is dependent on many factors such as, the specific compound employed, the plant species being treated, soil type, time of treatment, growth stage of plant at treatment, dosage of compound, formulation and a host of other such factors.

The substituted benzylquinuclidinum salts of the present invention are crystalline solids or oils, slightly soluble in water and appreciably soluble in common organic solvents.

The specific anion of the salts of the present invention is not critical. The anion can be any of the anions conventionally employed in plant growth regulators. The only limitation upon the anion chosen is that it be non-phytotoxic to the plants being treated. Representative anion include $Cl^{(-)}$, $Br^{(-)}$, $I^{(-)}$, $SCN^{(-)}$, $CH_3CO_2^{(-)}$, $C_2H_5CO_2^{(-)}$, $\phi SO_3^{(-)}$, $\phi CO_2^{(-)}$, $Cl\text{-}\phi\text{-}O^{(-)}$, $C_3H_7CO_2^{(-)}$, $SO_4^{(=)}$, $PO_4^{(\equiv)}$, $NO_3^{(-)}$, $ClO_3^{(-)}$, among others.

The compounds of the present invention can be prepared by the reaction of an appropriate substituted phenylalkyl halide (usually a chloride or bromide) and an appropriate quinuclidine in the presence of a solvent. The reaction can be characterized as follows:

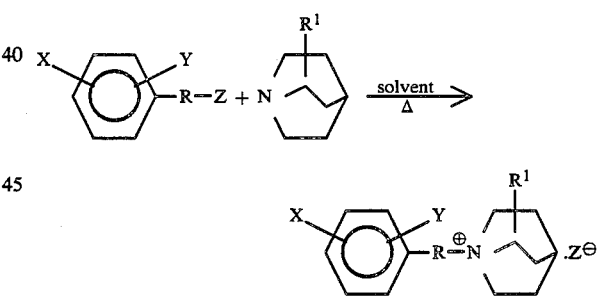

wherein Z is chlorine or bromine and X, Y, R and $R^1$ are as hereinabove defined. No attempt has been made to present a balanced equation.

In carrying out this reaction, the reactants and solvent are mixed together in any suitable fashion and the mixture maintained at about room temperature until the reaction is complete. The reaction period is from about 15 minutes to about 4 or 5 hours. The specific time period is dependent upon the specific reactants and solvents employed.

The amount of the reactants to be employed is not critical, some of the product being formed when employing any proportions. The reaction, however, consumes the reactants in the ratio of one mole of the phenylalkyl halide per mole of the quinuclidine reactant, the employment of such proportions is preferred.

It is preferred to employ polar solvents in carrying out this reaction. Representative solvents include, for example, water, acetone, acetonitrile, methanol, ethanol, n-propanol, isopropanol, n-butanol, isobutanol, t-butanol, nitromethane and methyl ethyl ketone. It is also within the scope of this invention to conduct the reaction in the absence of solvents provided that adequate control is maintained over the temperature.

Upon completion of the reaction, the product is removed from the reaction mixture. This separation can be achieved by (a) removing the solvent by evaporation under reduced pressure and recovering the product as a residue or (b) cooling the reaction mixture and mixing it with a solvent such as, for example, ethyl ether, hexane or mixtures thereof. If the product is solid, it can be separated by filtration or other known solid-liquid separation techniques; if the product is a liquid (oil), it can be separated by decantation or other conventional separation techniques. If desired, solid products can be further purified by recrystallization from solvents such as, for example, methyl ethyl ketone, ethyl acetate, ethyl ether, hexane, ethanol or mixtures thereof. The liquid products can sometimes be crystallized by trituration with the appropriate solvent.

While the above preparative procedures have been described wherein the product is in the form of the chloride or bromide salt, other salts can be prepared employing conventional procedures.

Such additional salts are prepared by treating the chloride or bromide product at room temperature in water with the alkali or alkaline earth salt of the organic or inorganic acid from which the desired anion is derived. This salt is of the formula $M^{\oplus} A^{\ominus}$ wherein M represents the alkali metals such as sodium, potassium, lithium, cesium or rubidium and the alkaline earth metals such as calcium, barium or strontium and A is as hereinbefore set forth. In addition, salts such as the fluoride salt can also be prepared by treatment with silver fluoride employing the above procedure. The above salts can also be prepared by passing the product bromide or chloride salt through an ion exchange column charged with the appropriate anion.

DESCRIPTION OF SOME PREFERRED EMBODIMENTS

The following examples illustrate the present invention and the manner by which it can be practical but, as such, should not be construed as limitations upon the overall scope of the same.

EXAMPLE I 1-((3-Trifluoromethyl)phenylmethyl) 1-Azonia bicyclo-[2.2.2]octane chloride

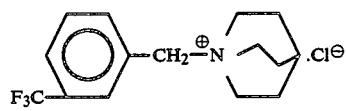

A solution of 50 grams (0.257 mole) of 3-(trifluoromethyl)benzyl chloride and 28.6 grams (0.257 mole) of quinuclidine in 300 milliliters of acetonitrile was stirred overnight at room temperature. The solvent was removed by evaporation under reduced pressure and the crude product was triturated with ethyl ether, filtered and dried. The above-named product was recovered by filtration in a yield of 71.8 grams as a white powder. The product was hydroscopic and melted at 130°–131° C. The structure of the compound was confirmed by NMR.

By following the preparative procedures as set forth in the above example and employing the appropriate starting reactants, the following compounds are prepared.

TABLE I

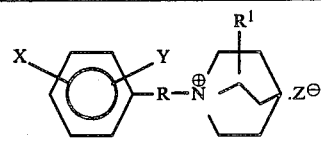

| Compound No. | X | Y | R | R¹ | Z | Melting Point °C. |
|---|---|---|---|---|---|---|
| 2 | H | 4-Br | —CH₂— | H | Cl | |
| 3 | H | 3-Cl | —CH₂— | H | Cl | 201–203 |
| 4 | H | 4-Cl | —CH₂— | H | Cl | 240–241 |
| 5 | H | 4-Br | —CH₂— | H | Br | 181–183 |
| 6 | H | 3-F | —CH₂— | H | Cl | 218–219 |
| 7 | H | 2,5-Cl₂ | —CH₂— | H | Cl | 229–230 |
| 8 | H | 4-Br | —CH₂— | H | Br | 253–254 |
| 9 | H | 4-Br | —CH₂CH₂— | H | Cl | |
| 10 | 3-CN— | 5-Cl | —CH(CH₃)— | H | EtCO₂ | |
| 11 | 4-CN— | H | —CH(CH₃)— | 3-CN | NO₃ | |
| 12 | 3-Hex— | 5-Cl | —CH₂CH₂— | 2-(=O) | SCN | |
| 13 | 4-Me— | H | —CH₂— | H | Cl | 250–252 |
| 14 | 3-Me— | H | —CH₂— | H | Cl | 172–173 |
| 15 | 3-Me— | H | —CH₂— | H | N₃ | |
| 16 | 3-CF₃S— | 5-I | —CH₂— | H | PO₄ | |
| 17 | 3-CF₃SO₂— | 5-I | —CH₂— | H | ClO₃ | |
| 18 | 4-CF₃— | H | —CH₂— | H | Cl | 112–114 |
| 19 | 5-CF₃— | 2-Cl | —CH₂— | H | Cl | 250–251 |
| 20 | 5-CF₃— | 2-Cl | —CH₂CH₂— | 3-COOMe | MeCO₂ | |

TABLE I-continued

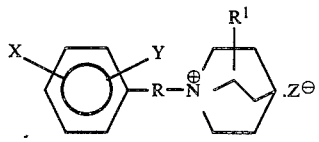

| Compound No. | X | Y | R | R$^1$ | Z | Melting Point °C. |
|---|---|---|---|---|---|---|
| 21 | 3-MeO— | H | —CH$_2$— | H | Cl | 133–135 |
| 22 | 3-n-BuO— | 4-F | —CH$_2$CH$_2$— | 3-COOMe | Cl | |
| 23 | 3,4-MD— | 2-Cl | —CH$_2$— | H | Cl | 257–258 |
| 24 | 3-MeS— | H | —CH$_2$— | H | Cl | 120–122 |
| 25 | 3-AmS— | 4-Br | —CH$_2$CH$_2$— | H | Br | |
| 26 | 3-PrO— | H | —CH$_2$— | H | Cl | 158–160 |
| 27 | 3-(CH≡CCH$_2$O—) | H | —CH$_2$— | H | Cl | 204–206 |
| 28 | 3-(CH$_2$=CHCH$_2$O—) | H | —CH$_2$— | H | Cl | 135–137 |
| 29 | 3-EtOC(O)CH$_2$O— | H | —CH$_2$— | H | Cl | 58–59 |
| 30 | 3-O—CH$_2$C(CH$_3$)$_2$—N=C— | H | —CH$_2$— | H | Br | 193–195 |
| 31 | 3-CO$_2$Me | H | —CH$_2$— | H | Br | 87–88 |
| 32 | 4-CO$_2$Et | 2-F | —CH$_2$CH$_2$— | 3-CN | PhCO$_2$ | |
| 33 | 3-CO$_2$Pr | H | —CH$_2$— | H | Br | 131–133 |
| 34 | 4-t-Bu | H | —CH$_2$— | H | Cl | 246–247 |
| 35 | 3-CN | H | —CH(CH$_3$) | H | Cl | |
| 36 | 3-CN | 4-Cl | —CH$_2$CH$_2$— | H | PhSo$_3$ | |
| 37 | 3-CN | H | —CH$_2$— | H | Br | 154–156 |
| 38 | 3-n-BuO | H | —CH$_2$— | H | Cl | 178–180 |
| 39 | 3-i-AmO | H | —CH$_2$— | H | Cl | 122–124 |
| 40 | H | 3-I | —CH$_2$— | H | Br | 222–224 |
| 41 | 3-EtS | H | —CH$_2$— | H | Cl | 138–140 |
| 42 | 3-PrS | H | —CH$_2$— | H | Cl | 129–131 |
| 43 | 3-Pro— | 4-Br | —CH$_2$— | H | Br | 129–131 |
| 44 | 3-CF$_3$O— | H | —CH$_2$— | H | Cl | 144–146 |
| 45 | 3-CF$_3$— | H | —CH$_2$— | 3-OH | Cl | 94–95 |
| 46 | 3-CF$_3$— | H | —CH$_2$— | 3-(=O) | Cl | 217–218 |
| 47 | 3-CF$_3$— | H | —CH$_2$— | 3-Cl | Cl | 91–93 |
| 48 | 2-CF$_3$— | H | —CH$_2$— | H | Cl | 120–125 |
| 49 | 3-CF$_3$— | H | —CH$_2$— | 3-OC(O)Me | Cl | 185–186 |
| 50 | 3-EtO— | H | —CH$_2$— | H | Cl | 166–168 |

In the above, the following abbreviations are employed.
Me = methyl
Et = ethyl
Pr = Propyl
Bu = Butyl
Am = Amyl
Hex = hexyl
Ph = phenyl
MD = Methylenedioxy It has been discovered that the compounds of the present invention can be employed as plant growth control agents. In this capacity, the compounds of this invention or compositions containing these compounds, as the active ingredient are useful in enhancing the growth of plants. The plants after treatment exhibit an increased growth and/or larger and/or more fruit and increased plant weight.

The compounds can be applied directly to the plant itself, i.e., above-ground surfaces of the plants, seeds, roots or tubers and the like.

The exposure of viable plants and plant parts to the action of a growth regulating amount of the compounds of the present invention is essential and critical for the practice of the present invention. The exact dosage to be employed, is not the same for all plants with all compounds and is dependent upon the response desired in the plant as well as such other factors as the plant species and the stage of growth at which treatment is made, and climatic conditions such as temperature, wind and especially rainfall.

In foliar treatments for the enhancement of the growth of germinant seeds, emerging seedlings and established vegetation, good results are obtained when from 0.002 pound to 5.0 pounds, preferably 0.01 to 2 pounds of the compounds are applied per acre.

The method of the present invention can be practiced by distributing the unmodified compounds upon the surfaces of the above-ground portion of plants. However, the present method also embraces the similar employment of liquid or dust compositions containing the compounds. In such usages, the compounds can be modified with one or a plurality of additaments or adjuvants including water or other liquid carriers, surface-active dispersing agents, and finely-divided solids. Depending upon the concentration of the compounds, such augmented compositions are adapted to be distributed upon the above-ground surfaces of plants, or to be employed as concentrates and subsequently diluted with additional inert carrier to produce the ultimate treating compositions. In compositions where the adjuvant or helper is a finely-divided solid, a surface-active agent or the combination of a surface-active agent, and a finely-divided solid, and/or a liquid additament, the adjuvant and/or adjuvants cooperate with the compounds so as to facilitate the invention and obtain an improved and outstanding result.

As indicated above, the compound can be directly applied to seeds prior to planting. The application to seeds of an effective growth enhancing dosage of the active compounds is essential and critical for the practice of the present invention. Good results are obtained when the seeds are treated with the compounds at a dosage of from about 0.0001 pound per hundred pounds of seed up to the phytotoxic threshold. The latter is about 0.1 pound per hundred pounds of seed inasmuch as lasting phytotoxic effects are obtaining with many plants at dosage levels above the 0.1 pound level. Depending on the particular plant species and variety and on the growing conditions some undesirable phytotoxic effects may be encountered even below the 0.1 pound level. Within the above set-forth treating range, the maximum growth enhancement response is obtained, and any phytotoxicity experienced in the very early stages of plant growth is usually overcome as the plant begins the growth and maturation habit which is characterized by the present process.

The treatment of the seeds may be accomplished by shaking or otherwise contacting the seeds with a dust composition containing the active agent, or by wetting the seeds with a liquid composition. In a convenient method of application, the compositions are applied in the form of dusts or sprays to the seeds as the latter are transported on the surface of a slowly moving belt or a perforated material such as a wire screen. In still another method, the required dosage of active agent can be applied on and about the seeds by the seed planting implement either in the hopper box or as the seeds are being planted into the soil or other growth media.

The exact concentration of the compounds to be employed in the treating compositions is not critical and may vary considerably provided the required dosage of the compounds is supplied upon the plant foliage. The concentration of the compound in liquid compositions employed to supply the desired dosage generally is from about 0.001 to 50 percent by weight although concentrations as low as 0.0001 percent and as high as 90 percent by weight are sometimes advantageously employed. In dusts, the concentration of toxicant is from about 0.1 to 90 percent by weight and usually not in excess of about 20 percent. In both liquid and dust compositions to be employed as concentrates, the compounds can be present in a concentration of from 5 to 98 percent by weight.

The quantity of treating compositions to be applied can vary considerably provided that the required dosage of the compound or active ingredient is applied in a sufficient amount of the finished composition to cover adequately the vegetation to be treated. In the treatment of seedlings good coverage is obtained when using from 1 to 60 gallons of finished spray composition per acre. Where large plants are concerned, it is frequently desirable to employ up to 600 gallons or more of the finished spray composition per acre to assure complete coverage of the above-ground portion of the vegetation. In the application of dusts to plant foliage, good results are obtained with from 40 to 2,000 pounds of finished dust per acre, the only requirement being that the required toxicant dosage be supplied in sufficient dust to achieve good coverage of the foliage.

Liquid compositions containing the desired amount of active ingredient can be prepared by dispersing the compounds in water or in organic liquid, with or without the aid of a suitable surface-active dispersing agent such as an ionic or non-ionic emulsifying agent. Suitable organic liquid carriers include the agricultural spray oils and the petroleum distillates such as diesel fuel, kerosene, fuel oil, and naphthas. The organic liquid compositions can contain a small amount of water as a solvent for the active ingredient. In such compositions, the carrier comprises an emulsion, namely, a mixture of water, emulsifying agent and organic liquid. In the liquid compositions, the choice of dispersing and emulsifying agent and the amount thereof employed is dictated by the nature of the composition and by the ability of the agent to facilitate the dispersion of the compounds in the carrier to produce the desired composition or to facilitate the wetting of surfaces upon which the compositions are applied. Dispersing and emulsifying agents which can be employed in the compositions include the condensation products of alkylene oxides with phenols and organic acids, alkyl aryl sulfonates, polyoxyalkylene derivatives or sorbitan esters, complex ether alcohols, mahogany soaps and the like.

In the preparation of dust compositions, the active ingredient is dispersed in and on a finely-divided solid such as clay, talc, chalk, gypsum, sugar, salt, bicarbonate, fertilizer and the like. In such operations, the finely-divided carrier is mechanically mixed or ground with the compounds. Similarly, dust compositions containing the compounds can be prepared from various of the solid surface-active dispersing agents such as bentonite, fuller's earth, attapulgite and other clays. Depending upon the proportion of ingredients, these dust compositions can be employed as concentrates and subsequently diluted with additional solid surface-active dispersing agent or with chalk, talc or gypsum, sugar, salt, fertilizer, and the like to obtain the desired amount of active ingredient in a composition adapted to be employed for the modification of the growth of plants. Also such dust compositions can be dispersed in water with or without the aid of a dispersing agent to form spray mixtures.

When operating in accordance with the present invention, growth enhancing amounts of the compounds are dispersed in any convenient fashion. The application of spray and dust compositions to the above-ground surfaces of plants can be carried out by conventional methods, e.g., power dusters, boom and hand sprayers and spray dusters.

The expression "surface-active dispersing agent" as herein employed is intended to include all agents which are capable of acting at the interfacial surface as the dispersion medium. Thus, the term is inclusive of the solid emulsifying agents such as finely-divided aluminum hydroxide and finely-divided bentonite, fuller's earth, attapulgite and other clays, as well as the ionic and non-ionic wetting and emulsifying agents such as the alkaline earth metal caseinates, alkyl aryl sulfonates, sulfonated oils, complex organic ester derivatives, complex ether alcohols, and the like.

The finely-divided inert solid or carrier as herein described refers to materials which are incapable of facilitating dispersion but which serve as a distribution medium for the active compounds. They include finely-divided materials such as chalk, talc, gypsum, sugar, salt, bicarbonate, fertilizers, and so forth.

EXAMPLE II

Tests were conducted to determine the effectiveness of various substituted phenylalkyl quinuclidinum compounds in increasing the growth of corn as evidenced by an increase in the dry weight of corn plants.

Seeds of the corn variety, Pioneer 3780, were planted in pots containing a mixture of soil and fertilizer. The seeded pots were maintained under normal greenhouse conditions. Two weeks after planting, the plants were at the 2-3 leaf stage. At this time, the plants were sprayed to run-off with various dilutions of the quinuclidinum compounds. The solutions were prepared by dissolving a predetermined amount of one of the compounds in a predetermined amount of water containing 0.1 percent of a wetting agent. There were 10 replications at each concentration of each compound and a set of untreated plants were maintained as controls.

After treatment, the plants were maintained under greenhouse conditions conducive to good plant growth. At the end of this period, the plants were cut off at the soil line and placed in a forced air oven at 100° C. for 48 hours. The dry weight of the plants was measured and the results calculated as a percent of control. These results, the compounds employed and the amounts employed are set forth below in Table II.

TABLE II

| Compound Number | Percent increase in dry weight of corn over controls at indicated dosage rates in parts of active compounds per million parts of the ultimate solution | |
|---|---|---|
| | 100 ppm | 10 ppm |
| 4 | 4 | 14 |
| | 4 | 23 |
| 6 | 30 | 7 |
| | 8 | 4 |
| 18 | 25 | 25 |
| 24 | 28 | 22 |
| 27 | 15 | 19 |
| 31 | 11 | 10 |

EXAMPLE III

Tests were conducted to determine the effectiveness of various substituted phenylalkyl quinuclidinum compounds in increasing the growth of corn as evidenced by an increase in the dry weight of corn plants.

Seeds of the corn variety, Pioneer 3780, were planted in pots containing a mixture of soil and fertilizer. The seeded pots were maintained under normal greenhouse conditions. Two weeks after planting, the plants were at the 2-3 leaf stage. At this time, the plants were sprayed to run-off with various dilutions of the quinuclidinum compounds. The solutions were prepared by dissolving a predetermined amount of one of the compounds in a predetermined amount of water containing 0.1 percent of a wetting agent. There were 10 replications at each concentration of each compound and a set of untreated plants were maintained as controls.

After treatment, the plants were maintained under greenhouse conditions conducive to good plant growth. At the end of this period, the plants were cut off at the soil line and placed in a forced air oven at 100° C. for 48 hours. The dry weight of the plants was measured and the results calculated as a percent of control. These results, the compounds employed and the amounts employed are set forth below in Table III.

TABLE III

| Compound Number | Percent increase in dry weight of corn over controls at indicated dosage rates in parts of active compound per million parts of the ultimate solution | | |
|---|---|---|---|
| | 25 ppm | 12 ppm | 6 ppm |
| 4 | 3 | 10 | 0 |
| 15 | 1 | 13 | 17 |
| | * | 19 | 7 |
| 18 | 20 | 22 | 24 |
| | 25 | 13 | 19 |
| 24 | 9 | 10 | 24 |
| 27 | 38 | 53 | 12 |

EXAMPLE IV

Seeds of the wheat cultivar Anza were grown in a greenhouse in pots whose soil consisted of ~97 percent sand. When the plants had 3-4 leaves, they were sprayed to the point of run-off with various dilutions of aqueous solutions of (Compound No. 1) 1-((3-trifluoromethyl)phenylmethyl)1-azonia bicyclo[2.2.2]octane chloride. These solutions were prepared by dissolving a predetermined amount of the compound in a predetermined amount of water containing 0.1 percent of a wetting agent. Untreated plants were maintained as controls. At the time of treatment, the plants were thinned to 5 plants per pot.

TABLE IV

| Concentration of Compound No. 1 in ppm | Height of plants as a percent of control | Weight of plants as a percent of control |
|---|---|---|
| 400 | −5 | +21 |
| 200 | +5 | +26 |
| 100 | +9 | +43 |
| 50 | +5 | +38 |

EXAMPLE V

Seeds of the wheat cultivar Anza were germinated on Whatman No. 1 filter paper in petri dishes using conventional techniques. After germination, the filter paper was saturated with an aqueous solution of compound No. 1. Untreated plants were maintained as controls. One week after treatment, the seedlings were measured to determine both its height and weight. The results of this examination is set forth below in Table V.

TABLE V

| Concentration of Compound No. 1 in ppm | Height of plants as a percent of control | Weight of plants as a percent of control |
|---|---|---|
| 5 | +9 | +24 |
| 1 | +11 | +25 |

What is claimed is:

1. A compound corresponding to the formula

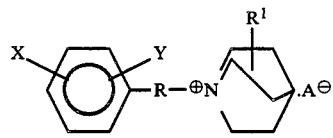

wherein
R represents methylene, ethylene or ethylidene;
$R^1$ represents hydrogen, hydroxy, chloro, bromo, fluoro, iodo, cyano, —$COOR^2$, oxo or acetoxy;
Y represents hydrogen, chloro, bromo, iodo or fluoro;
X represents hydrogen, alkyl of 1 to 6 carbon atoms, alkoxy of 1 to 6 carbon atoms, alkylthio of 1 to 6 carbon atoms, alkenyloxy of 2 to 6 carbon atoms, alkynyloxy of 2 to 6 carbon atoms, cyano, trifluoromethyl, (trifluoromethyl) thio, (trifluoromethyl)sulfonyl, trifluoromethoxy, —$COOR^2$ wherein $R^2$ is alkyl of 1 to 6 carbon atoms, —$C(O/S)NR^3R^4$ wherein $R^3$ represents $R^2$, alkenyl of 2 to 6 carbon atoms or alkynyl of 2 to 6 carbon atoms and $R^4$ represents $R^3$ or hydrogen, or —$S(O)_2NR^2R^3$ with the proviso that X and Y cannot both be hydrogen at the same time; and when X is cyano, or trifluoromethyl or Y is chloro, R is other than ethylene and when X is methyl, R is other than methylene and A represents a non-phytotoxic anion.

2. A compound as defined in claim 1 wherein R is methylene.

3. A compound as defined in claim 2 wherein X is alkoxy of 1 to 6 carbon atoms.

4. The compound as defined in claim 3 which is 1-((3-propoxy)phenylmethyl) 1-azonia bicyclo-[2.2.2]octane chloride.

5. A compound as defined in claim 2 wherein X is trifluoromethyl.

6. The compound as defined in claim 5 which is 1-((3-trifluoromethyl)phenylmethyl) 1-azonia bicyclo-[2.2.2]octane chloride.

7. A compound as defined in claim 2 wherein X is alkylthio of 1 to 6 carbon atoms.

8. The compound as defined in claim 7 which is 1-((3-methylthio)phenylmethyl) 1-azonia bicyclo-[2.2.2]octane chloride.

9. A compound as defined in claim 2 wherein Y is chloro.

10. The compound as defined in claim 9 which is 1-((4-chloro)phenylmethyl) 1-azonia bicyclo-[2.2.2]octane chloride.

11. A composition useful for treating plants to increase the growth of said plants which contains an inert carrier in admixture with as the active material, an effective plant growth regulating amount of a compound corresponding to the formula

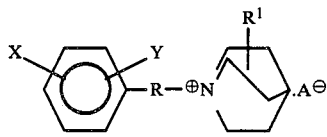

wherein
R represents methylene, ethylene or ethylidene;
$R^1$ represents hydrogen, hydroxy, chloro, bromo, fluoro, iodo, cyano, —$COOR^2$, oxo or acetoxy;
Y represents hydrogen, chloro, bromo, iodo or fluoro;
X represents alkyl of 1 to 6 carbon atoms, alkylthio of 1 to 6 carbon atoms, alkenyloxy of 2 to 6 carbon atoms, alkynyloxy of 2 to 6 carbon atoms, cyano, trifluoromethyl, (trifluoromethyl)thio, (trifluoromethyl) sulfonyl, trifluoromethoxy, —$COOR^2$ wherein $R^2$ is alkyl of 1 to 6 carbon atoms, —$C(O/S)NR^3R^4$ wherein $R^3$ represents $R^2$, alkenyl of 2 to 6 carbon atoms or alkynyl of 2 to 6 carbon atoms and $R^4$ represents $R^3$ or hydrogen, or —$S(O)_2NR^2R^3$ with the proviso that X nd Y cannot both be hydrogen at the same time; and that when X is cyano or trifluoromethyl or Y is chloro, R is other than ethylene and A represents a non-phytotoxic anion.

12. A composition as defined in claim 11 wherein R is methylene.

13. A composition as defined in claim 12 wherein X is alkoxy of 1 to 6 carbon atoms.

14. The composition as defined in claim 13 wherein the active compound is 1-((3-propoxy)phenylmethyl) 1-azonia bicyclo-[2.2.2]octane chloride.

15. A composition as defined in claim 12 wherein X is trifluoromethyl.

16. The composition as defined in claim 15 wherein the active compound is 1-((3-trifluoromethyl)phenylmethyl) 1-azonia bicyclo-[2.2.2]octane chloride.

17. A composition as defined in claim 12 wherein X is alkylthio of 1 to 6 carbon atoms.

18. The composition as defined in claim 17 wherein the active compound is 1-((3-methylthio)phenylmethyl) 1-azonia bicyclo-[2.2.2]octane chloride.

19. A composition as defined in claim 12 wherein Y is chloro.

20. The composition as defined in claim 19 wherein the active compound is 1-((4-chloro)phenylmethyl) 1-azonia bicyclo-[2.2.2]octane chloride.

21. The composition as defined in claim 12 in which the active material is present in the amount of from 0.0001 to 90 percent by weight of the ultimate composition.

22. A method for enhancing the growth of plants to obtain an increase in weight or size of said plants which comprises contacting plants or plant parts or their habitat with a growth enhancing amount of a composition containing as the active material a compound corresponding to the formula

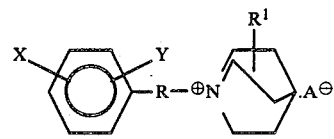

wherein
R represents methylene, ethylene or ethylidene;
$R^1$ represents hydrogen, hydroxy, chloro, bromo, fluoro, iodo, cyano, —$COOR^2$, oxo or acetoxy;
Y represents hydrogen, chloro, bromo, iodo or fluoro;
X represents hydrogen alkyl of 1 to 6 carbon atoms, alkylthio of 1 to 6 carbon atoms, alkenyloxy of 2 to 6 carbon atoms, alkynyloxy of 2 to 6 carbon atoms, cyano, trifluoromethyl, (trifluoromethyl)thio, (trifluoromethyl)sulfonyl, trifluoromethoxy, —$COOR^2$ wherein $R^2$ is alkyl of 1 to 6 carbon atoms, —$C(O/S)NR^3R^4$ wherein $R^3$ represents $R^2$, alkenyl of 2 to 6 carbon atoms or alkynyl of 2 to 6 carbon atoms and $R^4$ represents $R^3$ or hydrogen, or —$S(O)_2NR^2R^3$ and with the proviso that X and Y cannot both be hydrogen at the same time A represents a non-phytotoxic anion.

23. The method as defined in claim 21 wherein R is methylene.

24. A method as defined in claim 23 wherein X is alkoxy of 1 to 6 carbon atoms.

25. The method as defined in claim 24 wherein the active compound is 1-((3-propoxy)phenylmethyl) 1-azonia bicyclo-[2.2.2]octane chloride.

26. A method as defined in claim 23 wherein X is trifluoromethyl.

27. The method as defined in claim 26 wherein the active compound is 1-((3-trifluoromethyl)phenylmethyl) 1-azonia bicyclo-[2.2.2]octane chloride.

28. A method as defined in claim 23 wherein X is alkylthio of 1 to 6 carbon atoms.

29. The method as defined in claim 28 wherein the active compound is 1-((3-methylthio)phenylmethyl) 1-azonia bicyclo-[2.2.2]octane chloride.

30. A method as defined in claim 23 wherein Y is chloro.

31. The method as defined in claim 30 wherein the active compound is 1-((4-chloro)phenylmethyl) methyl) 1-azonia bicyclo-[2.2.2]octane chloride.

32. The method as defined in claim 22 in which plant seeds are contacted.

33. The method as defined in claim 22 in which the above-ground portions of the plants are contacted.

34. The method as defined in claim 32 wherein the seeds are contacted with from 0.0001 to 0.1 pound of the active material per 100 pounds of seed.

35. The method as defined in claim 33 wherein the above-ground portions of the plants are contacted with from 0.002 pound to 5.0 pounds of the active material per acre.

* * * * *